(12) United States Patent
Barlag et al.

(10) Patent No.: US 8,105,478 B2
(45) Date of Patent: Jan. 31, 2012

(54) METHOD FOR MEASURING THE CONCENTRATION OR CHANGE IN CONCENTRATION OF A REDOX-ACTIVE SUBSTANCE AND CORRESPONDING DEVICE

(75) Inventors: Heike Barlag, Nürnberg (DE); Walter Gumbrecht, Herzogenaurach (DE); Konrad Mund, Uttenreuth (DE)

(73) Assignee: Siemens Aktiengesellschaft, Munich (DE)

( * ) Notice: Subject to any disclaimer, the term of this patent is extended or adjusted under 35 U.S.C. 154(b) by 1069 days.

(21) Appl. No.: 10/587,837

(22) PCT Filed: Jan. 26, 2005

(86) PCT No.: PCT/EP2005/050333
§ 371 (c)(1),
(2), (4) Date: Apr. 10, 2007

(87) PCT Pub. No.: WO2005/073708
PCT Pub. Date: Aug. 11, 2005

(65) Prior Publication Data
US 2008/0099347 A1    May 1, 2008

(30) Foreign Application Priority Data
Jan. 29, 2004  (DE) .................... 10 2004 004 654

(51) Int. Cl.
*G01N 27/26* (2006.01)
*G01N 33/53* (2006.01)
*G01N 33/487* (2006.01)

(52) U.S. Cl. .................. 205/793.5; 205/777.5; 204/450; 435/6.1; 435/287.2; 435/7.1; 436/501; 436/86; 436/94; 436/63; 436/2; 422/68.1; 422/82.01

(58) Field of Classification Search ..... 204/400–403.14, 204/406, 450; 205/775, 777.5, 793.5; 436/501, 436/86, 94, 63, 2; 435/6.1, 287.2, 7.1; 422/68.1, 422/82.01
See application file for complete search history.

(56) References Cited

U.S. PATENT DOCUMENTS
4,897,162 A * 1/1990 Lewandowski et al. ...... 205/786
(Continued)

FOREIGN PATENT DOCUMENTS
DE    43 35 241 A1    4/1995
(Continued)

OTHER PUBLICATIONS
Gunasingham et al. (J. Electroanal. Chem. 287, 1990, 349-362).*
(Continued)

*Primary Examiner* — Jeffrey T Barton
*Assistant Examiner* — Jennifer Dieterle
(74) *Attorney, Agent, or Firm* — Harness, Dickey & Pierce, P.L.C.

(57) ABSTRACT

In order to follow the change in concentration of a redox-active substance, potential suitable for a reducing process or oxidation process are applied to the working electrode of a measuring device. The potential of the working electrode is pulsed and measuring phases and relaxation phases are alternately produced, the pulse lengths of the measuring phase and relaxation phase being predetermined in a suitable manner. In this manner, a rapid relaxation of the concentration gradient is forced electrochemically so that the measurement can be carried out on simple transducer arrays. The device includes a transducer array in addition to a suitable potentiostat. The transducer array may include a planar metal substrate on which at least one flexible insulator having a firm connection between the metal surface and the insulator surface is located. The array is generated by suitably structuring the substrate.

16 Claims, 7 Drawing Sheets

U.S. PATENT DOCUMENTS

| | | | |
|---|---|---|---|
| 6,391,558 B1 * | 5/2002 | Henkens et al. | 435/6 |
| 2002/0195345 A1 | 12/2002 | Bentsen | |
| 2004/0063152 A1 * | 4/2004 | Gumbrecht et al. | 435/7.1 |

FOREIGN PATENT DOCUMENTS

| | | | |
|---|---|---|---|
| DE | 4335241 A1 | | 4/1995 |
| DE | 199 17 052 | | 10/2000 |
| DE | WO0242759 | * | 5/2002 |
| EP | 0 396 788 A1 | | 5/1989 |
| EP | 0396788 A | | 11/1990 |
| US | WO 01/21827 | * | 3/2001 |
| WO | WO 91/08474 | | 6/1991 |
| WO | WO 99/49934 | | 10/1999 |
| WO | WO 01/21827 | | 3/2001 |
| WO | WO 01/21827 A | | 3/2001 |
| WO | WO 01/21827 A1 | | 3/2001 |
| WO | WO 03/043945 | | 5/2003 |
| WO | WO 2004/001404 | | 12/2003 |

OTHER PUBLICATIONS

Bindra et al. (Anal. Chem. 1989, 61 2566-2570).*

Gunasingham Hari et al.: "Pulsed Amperometric Detection of Glucose using a Mediated Enzyme Electrode", J. Electroanal. Chem . . . Interfacial Electrochem: Journal of Electroanalytical Chemistry and Interfacial Electrochemistry. Jul. 25, 1990, Bd. 287, Nr. 2, S. 349-362.

Office Action dated Apr. 10, 2008 in corresponding UK Patent Application No. 0617003.9.

Gunasingham, Hari, et al., "Pulsed amperometric detection of glucose using a mediated enzyme electrode," *J. Electroanal. Chem.*, 287, pp. 349-362 (1990) (Elsevier Sequoia S.A.).

Gunasingham Hari et al.: "Pulsed amperometric detection of glucose using a mediated enzyme electrode" J Electroanal Chem Interfacial Electrochem; Journal of Electroanalytical Chemistry and Interfacial Elctrochemistry, Jul. 25, 1990.

German Office Action dated Jun. 14, 2007.

Bard, Allen J. and Larry R. Faulkner. Electrochemical Methods, Fundaments and Applications. John Wiley & Sons, Inc. 2001. pp. 293-299, 287, 648.

* cited by examiner

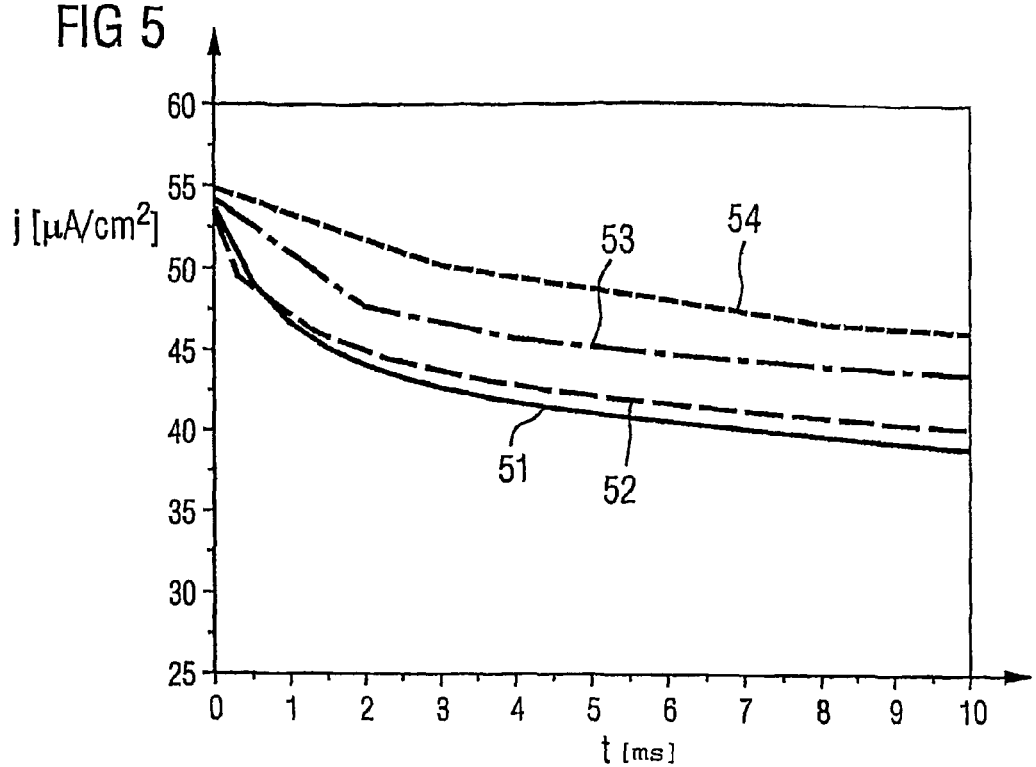
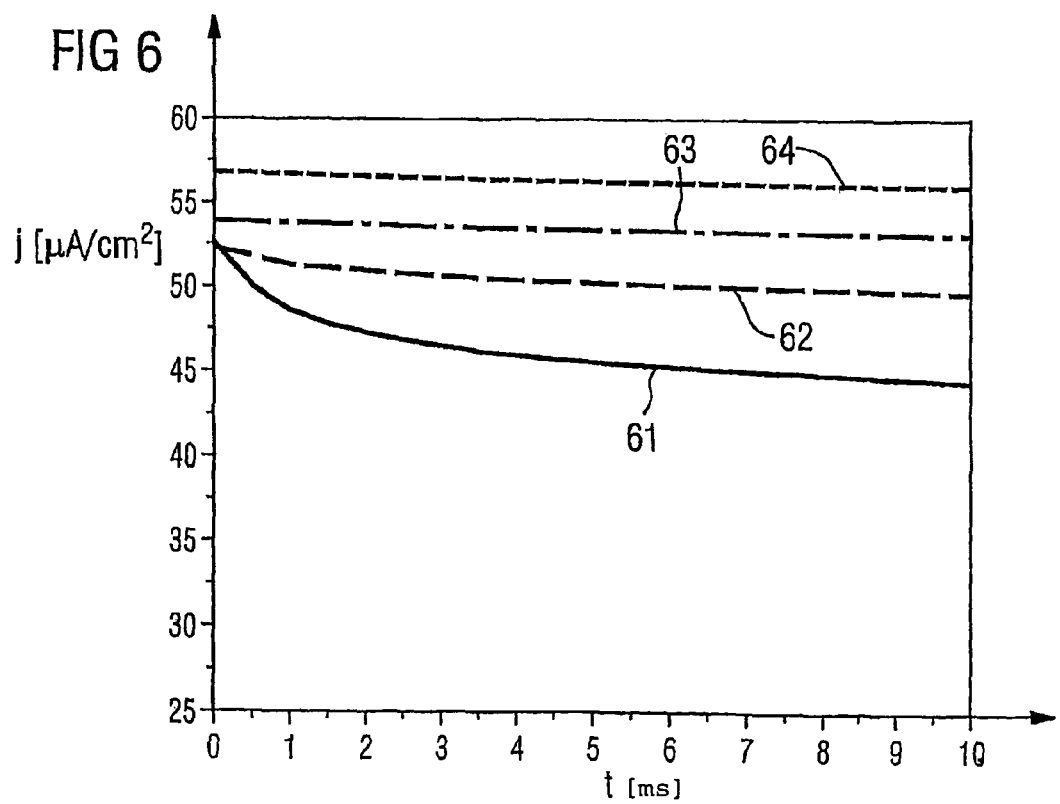

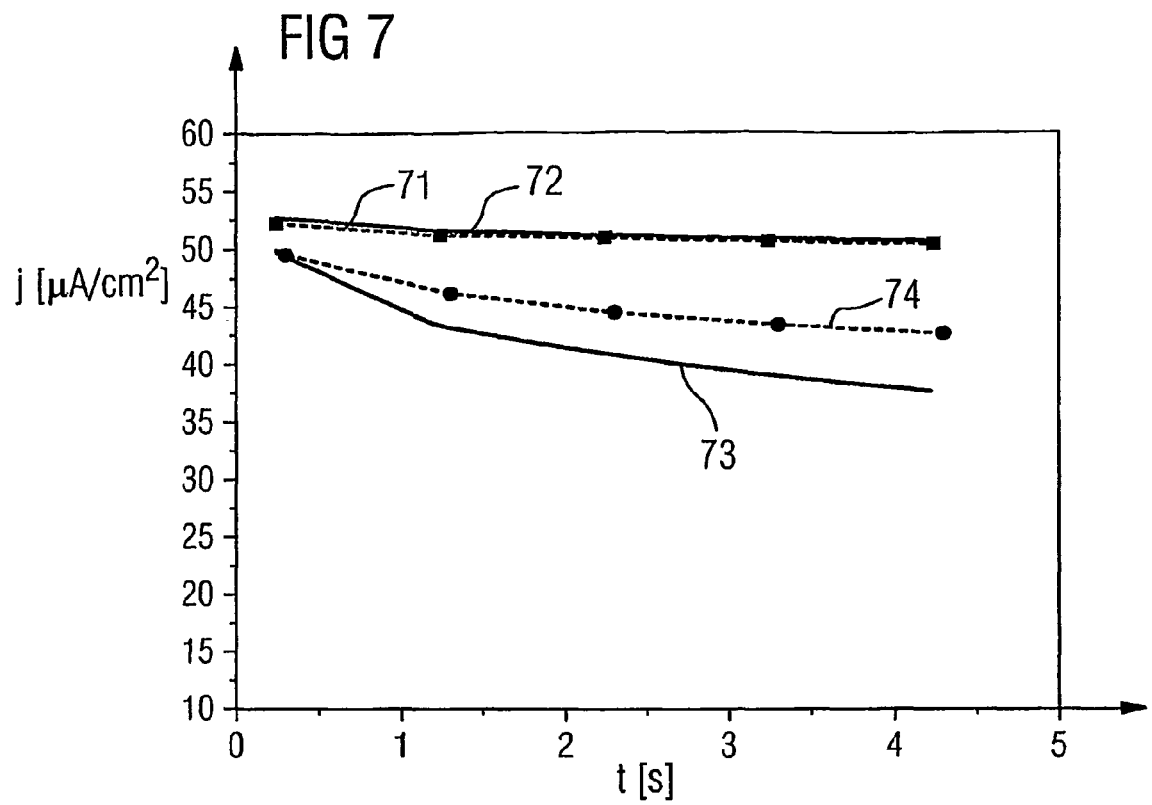
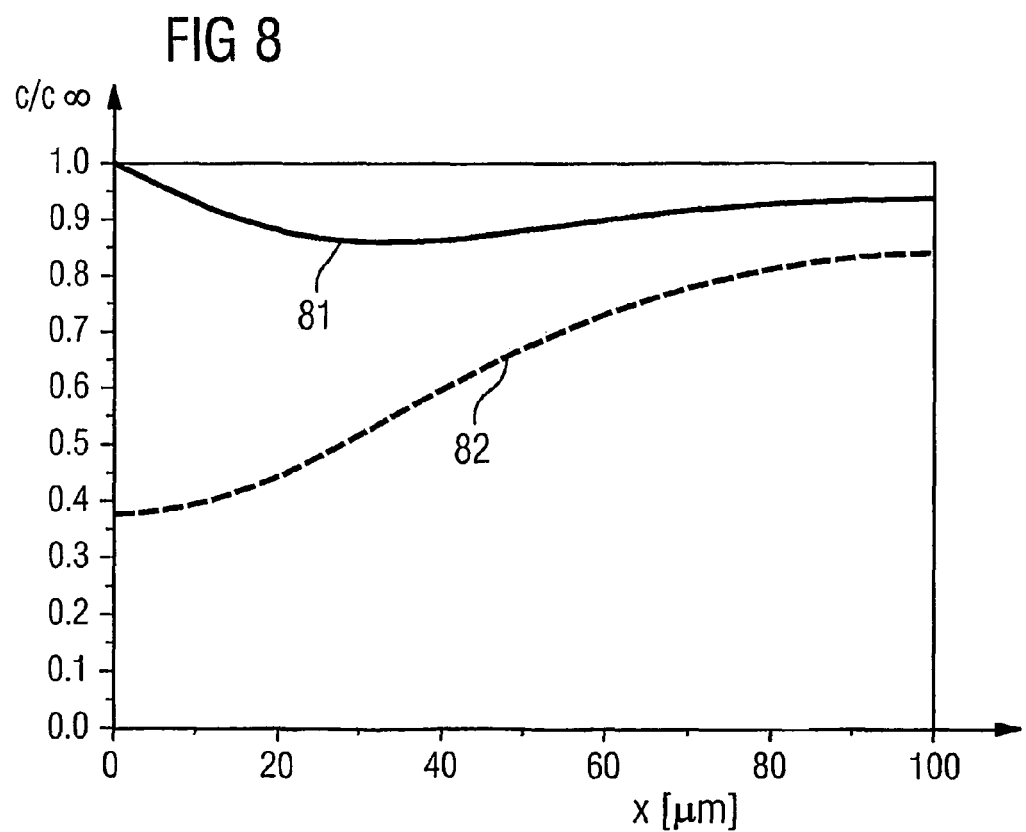

METHOD FOR MEASURING THE CONCENTRATION OR CHANGE IN CONCENTRATION OF A REDOX-ACTIVE SUBSTANCE AND CORRESPONDING DEVICE

This application is the national phase under 35 U.S.C. §371 of PCT International Application No. PCT/EP2005/050333 which has an International filing date of Jan. 26, 2005, which designated the United States of America and which claims priority on German Patent Application number 10 2004 004 654.9 filed Jan. 29, 2004, the entire contents of which are hereby incorporated herein by reference.

FIELD

The invention generally relates to an electrochemical measuring method for measuring the concentration or change in concentration of a redox-active substance. In addition, the invention also generally relates to an associated device, such as one for carrying out the measuring method for example, with an electrochemical transducer array.

BACKGROUND

Amperometric sensors are based on the simple principle that reducible or oxidizable substances can be converted by applying a corresponding potential to an electrode. The so-called Faraday current that then flows is a measure of the concentration of this substance. This current cannot, however, be measured directly after the potential has been applied, because above all a high capacitive current flows in the first instance. This is brought about by the charge-reversal of the double layer of the electrode. It dies down exponentially with time.

The Faraday current is likewise reduced with time, since as a result of the substance-conversion, a depletion takes place in front of the electrode. The subsequent delivery of substance from the solution to the electrode takes place solely as a result of diffusion in the case of non-stirred, that is, non-convective systems. Concentration profiles set in the solution. With sufficiently positive potentials (oxidation) or negative potentials (reduction), the Cotrell equation holds good for the time-dependence of the current:

$$I = nFA \frac{\sqrt{D}}{\sqrt{\pi t}} c_\infty, s \rightarrow \infty \qquad (1)$$

The significations in this connection are:
n: number of electrons per formula conversion
F: Faraday constant
A: area of the electrode
D: diffusion coefficient
$c_\infty$: concentration of the substance to be converted in the solution
s: extent of the electrolyte space in front of the electrode Equation (1) implies that the Faraday current diminishes with the reciprocal square root of time, that is, more slowly than the capacitive current. Some time after the change in the potential, the current is therefore mainly determined by the Faraday current. For each system it is necessary to find a point in time at which the capacitive current is low, yet the Faraday current is still as high as possible.

One possibility for determining very small concentrations ($10^{-10}$ mol/l) is voltammetric stripping analysis. In this connection, by applying a suitable potential the substance that is to be determined is first enriched by that of the electrode. In a second step, the quantity of substance on the electrode is then determined [W. Buchberger, Elektrochemische Analyseverfahren, Heidelberg Berlin: published by Spektrum Akademischer Verlag in 1998 and DE 44 24 355]. This method does not enable there to be any time resolution on account of the two method steps. Changes in concentration cannot therefore be tracked or can only be tracked very slowly.

A further analytical standard method for determining very small concentrations is polarography [Rach & Seiler, Polarographie u. Voltametrie in der Spurenanalytik, Heidelberg: Hüthig 1984]. Here concentrations in the order of magnitude of $10^{-9}$ mol/l can be measured with suitable pulse methods and with the use of a so-called "Dropping Mercury Electrode" (DME). In the case of the DME, use is made inter alia of the fact that each drop of mercury plunges into the solution anew and the concentration $c_\infty$ is found there again. In the case of a static electrode, however, this is not the case. After each measurement it would be necessary to wait for so long until the concentration profile is relaxed by the diffusion process. Depending on the magnitude of the diffusion coefficient, if there is no stirring this process can take a few seconds. If the waiting time is not long enough, the current will diminish from measurement to measurement, since the initial concentration drops in front of the electrode.

In the case of some applications, however, it can be necessary to determine the concentration in rapid succession, if, for example, a change in concentration is to be observed. One possible area of use is that of tracking the enzymatic formation of a mediator in molecular-biological detection systems.

In the case of biochemical sensors, molecular recognition systems, for example haptens, antigens or antibodies, are placed on or in the vicinity of the electrodes. The target molecule binds thereto and is provided with an enzyme label either directly or by way of intermediate steps. If the corresponding enzyme substance is now added, the enzyme releases a substance that can be detected. This happens either visually or electrochemically. This is the so-called ELISA-test (Enzyme Linked Immuno Sorbent Assay). DNA analysis methods can also be carried out in a similar way.

In the case of electrochemical detection, it is advantageous to detect not just the absolute concentration of the measured variable, referred to as a "mediator", for the electrochemical conversions specified above, but also the change, in particular the increase, in the concentration over a few seconds. As a result, the influence of different states of the biochemical system is eliminated at the start of the measurement. The time resolution of such a measurement must then amount to 1 to 2 Hz in order to be useful technically and economically.

Specifically in the case of redox-active substances up until now it has been possible to employ so-called redox-cycling with the use of interdigital electrodes. In so doing, use is made of the fact that the substance that is oxidized at one electrode can be reduced again at the second electrode. The electrodes are then constantly set to the oxidation or reduction potential. To this end, the two interdigital electrodes with electrode fingers interlocking in a chamber-like manner are connected together with the reference electrode and a counter electrode to a bipotentiostat [O. Niwa, M. Morita, H. Tabei, Anal. Chem. 62 (1991), 447-452 and DE 43 18 519 A1].

A precondition for redox-cycling is that the distance between the electrodes, that is, the electrode fingers of the interdigital electrodes that are associated with each other, lies in the order of magnitude of the diffusion-layer thickness, that is, in the region of a few µm. On the basis of the concentration profiles, in addition to the concentration and the diffusion coefficient the number of electrode fingers and their length enter into the measured current [K. Aoki, J. Electroanal. Chem, 270 (1989), 35]. It follows from this that the necessary structures must be very fine and expensive to produce.

The monograph "Electrochemical Methods, Fundamentals and Applications", John Wiley & Sons, 1980, provides a general overview of electrochemical measuring technology. Further references to measurement specifically with respect to liquids or even for biochemical measurements are given in DE 43 35 241 A1, in DE 41 31 731 A1, in DE 197 17 809 U1 and DE 199 17 052 A1. A method for electrochemically measuring redox-cycling with a practice-related electrode arrangement is described in detail in WO 01/67587 A1.

SUMMARY

In at least one embodiment of the invention, a method is put forward in which the determination of concentrations of a redox-active substance in μm-concentrations is possible on areal electrodes with diameters of ≧30 μm, preferably ≧50 μm. In this connection, the system is not to be convective, that is, neither the electrode nor the solution is to be stirred or moved, and the measuring frequency is to amount to ≧1 Hz. In addition, an associated measuring device is to be provided.

It is proposed that the potential of the working electrode be pulsed in a manner known per se. In the case of at least one embodiment of the invention, however, measuring phases and also relaxation phases are formed alternately, with the measuring-phase pulse lengths being selected so that towards the end of the pulse the capacitive current is small in comparison with the Faraday current, and with the relaxation-phase pulse lengths being selected so that towards the end of the pulse the concentration gradient is relaxed so that at the beginning of the following measuring phase the change in concentration of the mediator, brought about by the consumption of the mediator by the measurement itself, is reversed to the greatest possible extent. Thus, the current that is measured at the end of the measuring phase forms a significant measuring signal.

In accordance with at least one embodiment of the invention, rapid measurement of the concentration and in particular of the change in concentration of a mediator in molecular-biological detection systems by way of the electrochemical redox-reaction of the enzymatically formed redox-active substance, where the working electrodes are anchored in caverns on a chip band, is effected by cyclic pulse-loading, with the current that is measured after the charge-reversal of the double layer has died down forming the measuring signal.

A basis of at least one embodiment of the invention is the recognition that by using a new redox-cycling variant advantageously it is possible to carry out measurements at electrodes with diameters in the order of magnitude of a few 100 μm up to 1 cm. Complexly constructed interdigital electrodes are no longer necessary. Now inexpensive transducer arrays can be used, as described in detail in particular in Patent Application Ser. No. 10 2004 004 654.9-52 belonging to the applicant and having the same filing priority, the entire contents of which is hereby incorporated herein by reference.

In the case of the associated measuring device, the measuring installation is simplified with respect to redox-cycling to the effect that no bipotentiostat is required. One single potentiostat in combination with a pulse generator suffices.

In the case of at least one embodiment of the invention, it is not a stationary state—as in the case of "normal" redox-cycling—that is set, but instead a rapid relaxation of the concentration gradient that is forced electrochemically. To this end, the potential of the working electrode is pulsed. A diffusion layer is formed whose thickness at the end of the measuring period attains a maximum value that is dependent upon the length of the measuring phase.

When measuring oxidation currents, an adequate reduction potential is set during the relaxation phase. The species oxidized during the measuring phase and still located in front of the electrode are therefore reduced again. The concentration gradient and thus the diffusion layer are broken down. Instead of therefore, as in the case of redox-cycling, establishing constant diffusion-layer thicknesses, in the case of pulsed redox-cycling in accordance with the invention the diffusion layer is built up and broken down again with time.

In both cases, as a result a diffusion-layer thickness is set that is limited at least in terms of its maximum value. If a reduction is to be observed, the reduction potential must be set during the measuring phase and the corresponding oxidation potential must be set during the relaxation phase.

BRIEF DESCRIPTION OF THE DRAWINGS

Further details and advantages of the invention emerge from the following description, with reference to the figures, of example embodiments in connection with the claims and with the aid of the drawings, in which:

FIG. 5 shows a graphic representation of the dependence of the current density upon time;

FIG. 6 shows a representation in accordance with FIG. 5 for the relaxation phase;

FIG. 7 shows a representation in accordance with FIG. 5 with comparison of experimental and calculated values;

FIG. 8 shows a graphic representation of the dependence of the concentration upon the electrode spacing;

DETAILED DESCRIPTION OF THE EXAMPLE EMBODIMENTS

Figure 10:
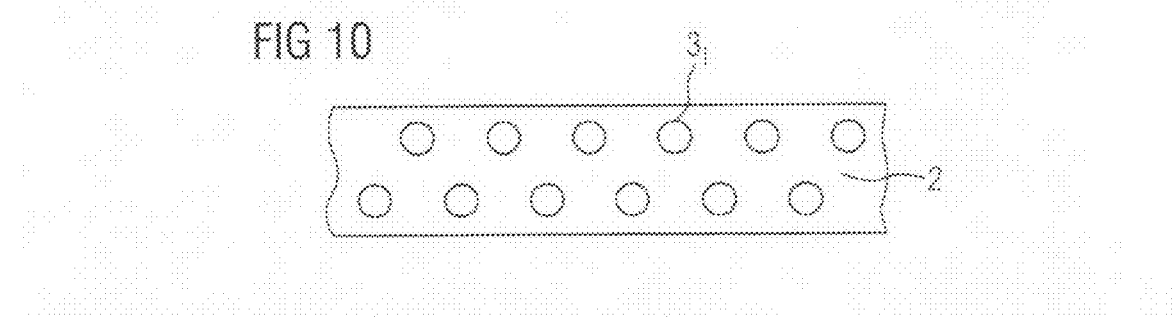
FIGS. 10/11 show the transducer array for the measuring device in accordance with FIG. 9 in the view from above and below.
Figure 11:
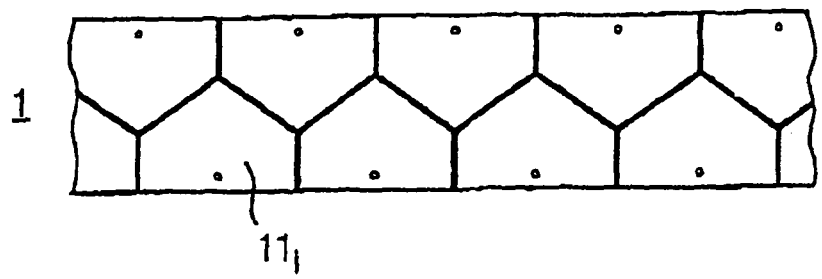
Figure 12:
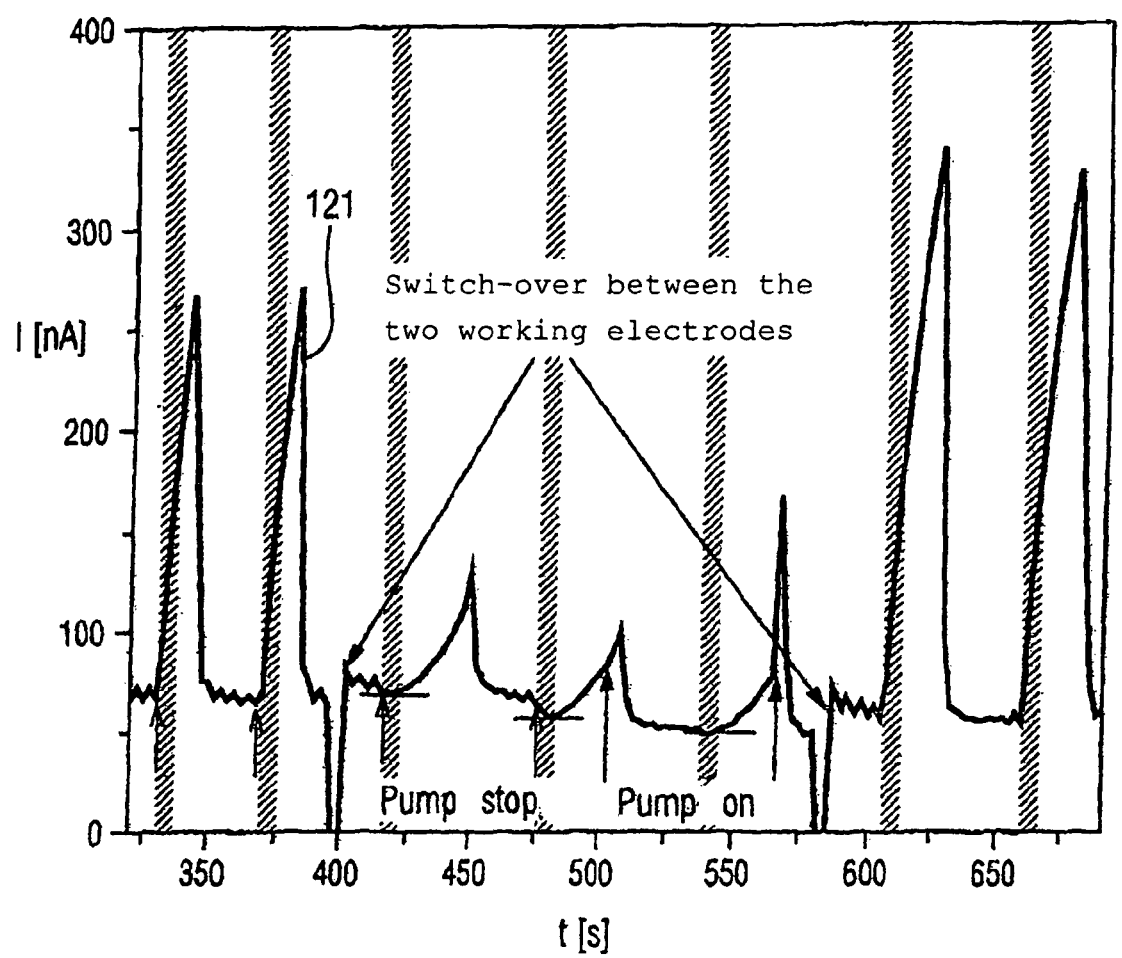
FIG. 12 shows the course of a typical measurement with a measuring-current curve.

The methodology of pulsed redox-cycling is described in the first instance in FIGS. 1 to 4. In this connection, it is assumed that the methodology of redox-cycling is known per se from the prior art. Then with reference to FIGS. 5 to 8 observations are made with regard to the accuracy, and finally in FIG. 9 a measuring device with an example transducer array, whose structure is shown in FIGS. 10 and 11, is specified. Finally, FIG. 12 depicts the direction of the method when the arrangement is used as a DNA sensor.

Figure 1:
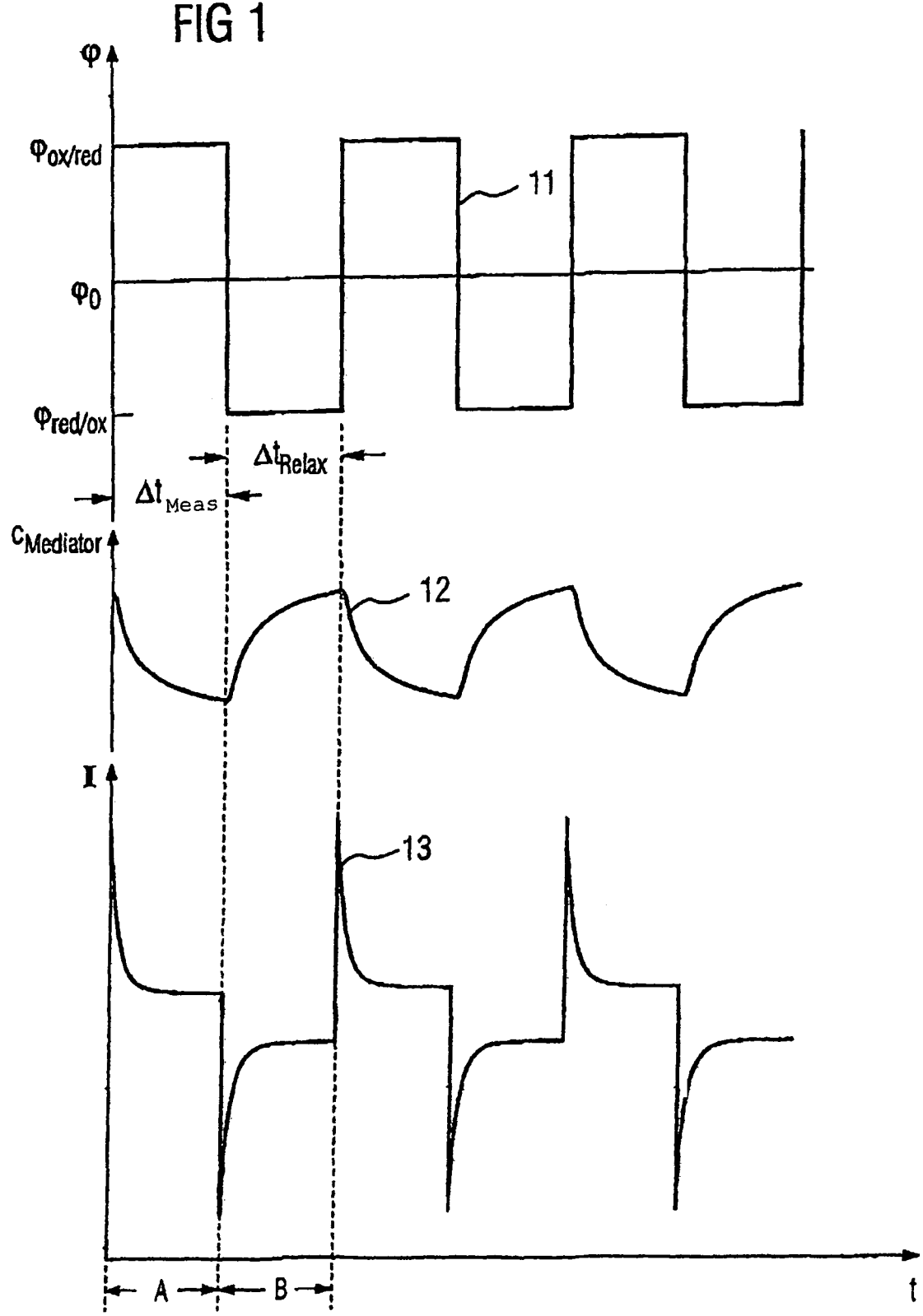
FIG. 1 shows a graphic representation of pulsed redox-cycling with characteristic lines for pulse lengths and associated concentration and signal curves.

The different phases during measurement are characterised in FIG. 1. Which is the measuring phase and which is the relaxation phase depends upon whether an oxidation current or a reduction current is to be measured. The pulse lengths for oxidation and reduction need not be the same, that is, the times $\Delta t_{ox}$ and $\Delta t_{red}$ can differ. In addition, the potentials $\phi_{ox}$ and $\phi_{red}$ need not be symmetrical with respect to the redox-potential $\phi_0$ of the species.

The representation of FIG. 1 shows the possible course of the potential with the use of rectangular pulses. In this connection, the potentials $\phi_{ox}$ $\phi_{red}$ and the times $\Delta t_{ox}$ and $\Delta t_{red}$ are plotted in arbitrary units with the pulse shape 11. The pulse shape 11 with the pulse lengths for oxidation and reduction does not need to be symmetrical. Pulsed redox-cycling can be realized in exactly the same way with delta voltage curves or sine curves.

In particular, in FIG. 1 the measuring phase is denoted by A and the relaxation phase is denoted by B. Besides the potential curve 11, a curve 12 for the concentration of the mediator of the electrode and in addition to this the electric current 13 as a measuring signal are further represented. The current value that is relevant for the process is therefore present at the respective end of the relaxation interval and is a measure of the relaxed change in concentration.

In the case of the further observations that are made it is assumed that the concentration of a molecule that is present in its reduced form is to be measured. In this case, during the measuring phase the potential is related in a positive way to the redox potential of the species. The highest measurement currents are achieved if the potential lies so far in the positive area that a diffusion limiting current sets in. The current is then not limited by the kinetics of the redox reaction, but just by the diffusion. The development of the concentration profile of the reduced species over time follows from the corresponding solution of Fick's laws of diffusion in the simple infinite half-space.

$$c(t, x) = c_\infty \cdot erf\left(\frac{x}{2\sqrt{Dt}}\right), s \to \infty \quad (2)$$

Figure 2:
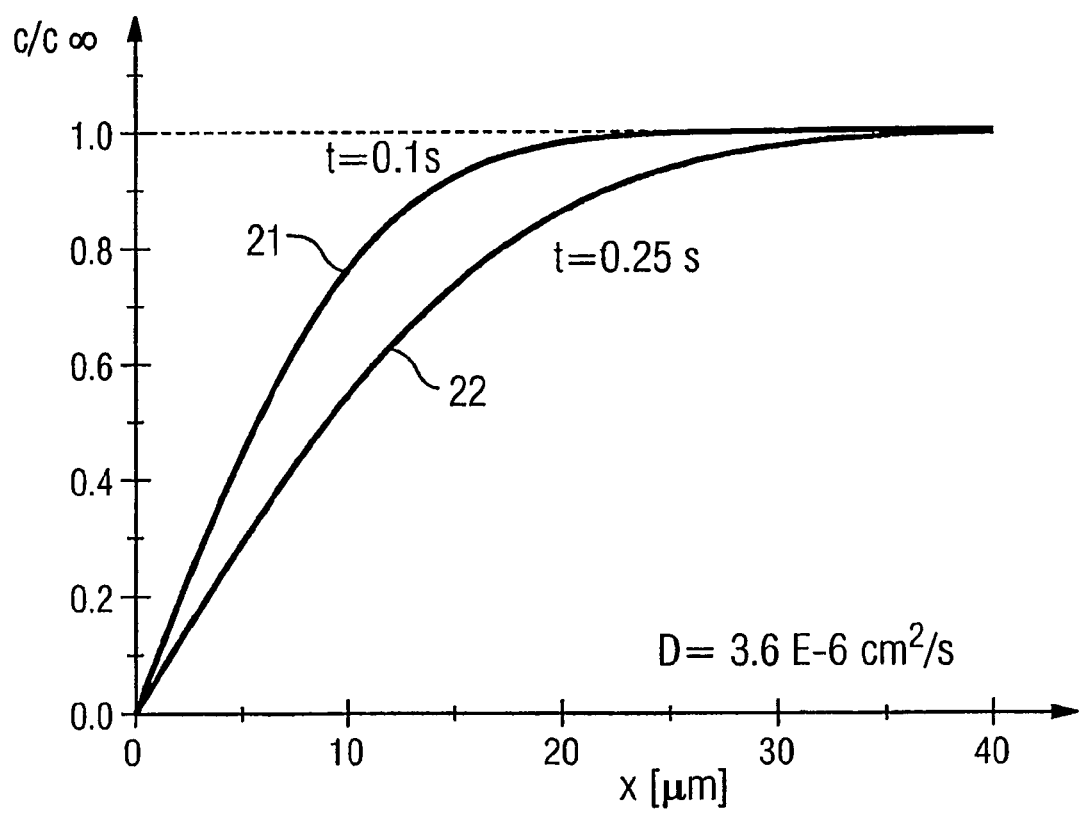
FIG. 2 shows a graphic representation of the dependence of the relative concentration upon the spacing of the electrodes.

The significations in this connection are:
c: concentration as a function of time and place
$c_\infty$: concentration in the solution ($x \to \infty$)
erf: error function
D: diffusion coefficient
s: extent of the electrolyte space in front of the electrode Two concentration profiles 21 and 22 for a substance with the diffusion coefficient D=3.6 E–6 cm$^2$/s are shown in FIG. 2. This corresponds to the diffusion coefficient of para-aminophenol (pAP), by way of the example of which the mode of operation of pulsed redox-cycling shall be demonstrated below.

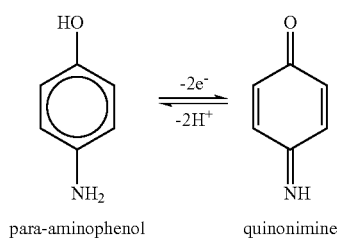

para-aminophenol      quinonimine

After 0.1 s, the diffusion layer has a thickness of approximately 25 μm. After 0.25 s, the extent of the layer depleted with respect to pAP already amounts to 40 μm. The thicker this layer is, the longer the relaxation lasts as a result of diffusion.

Figure 3:
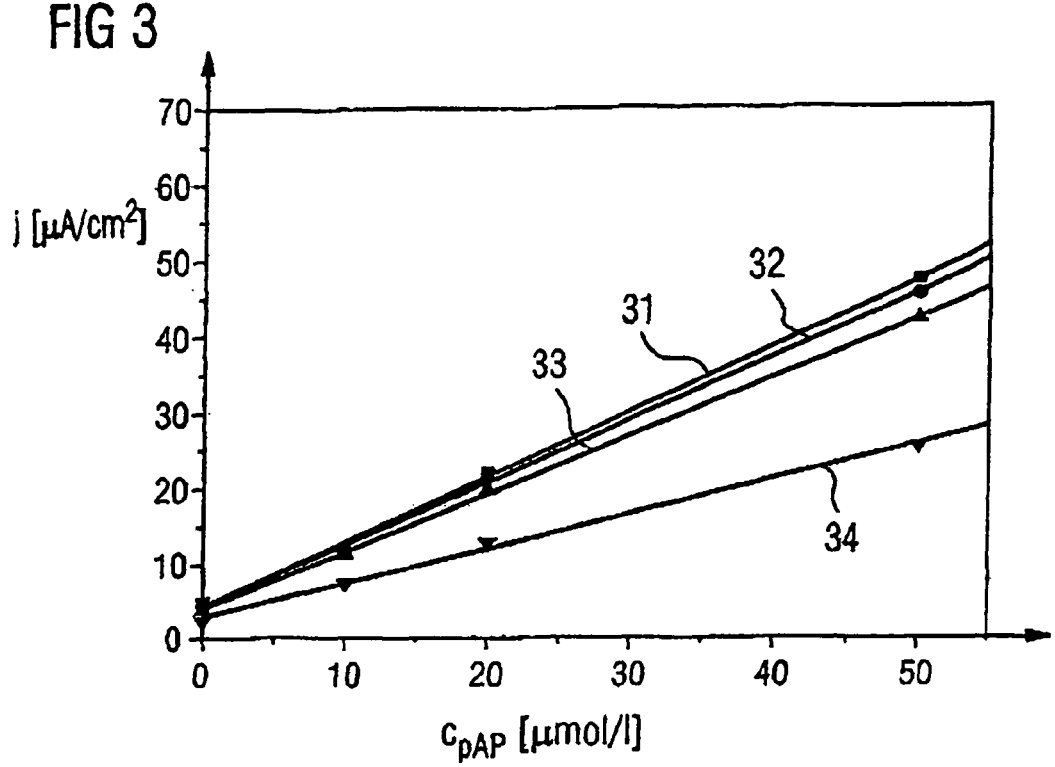
FIG. 3 shows a graphic representation of the current of the concentration.
Figure 4:
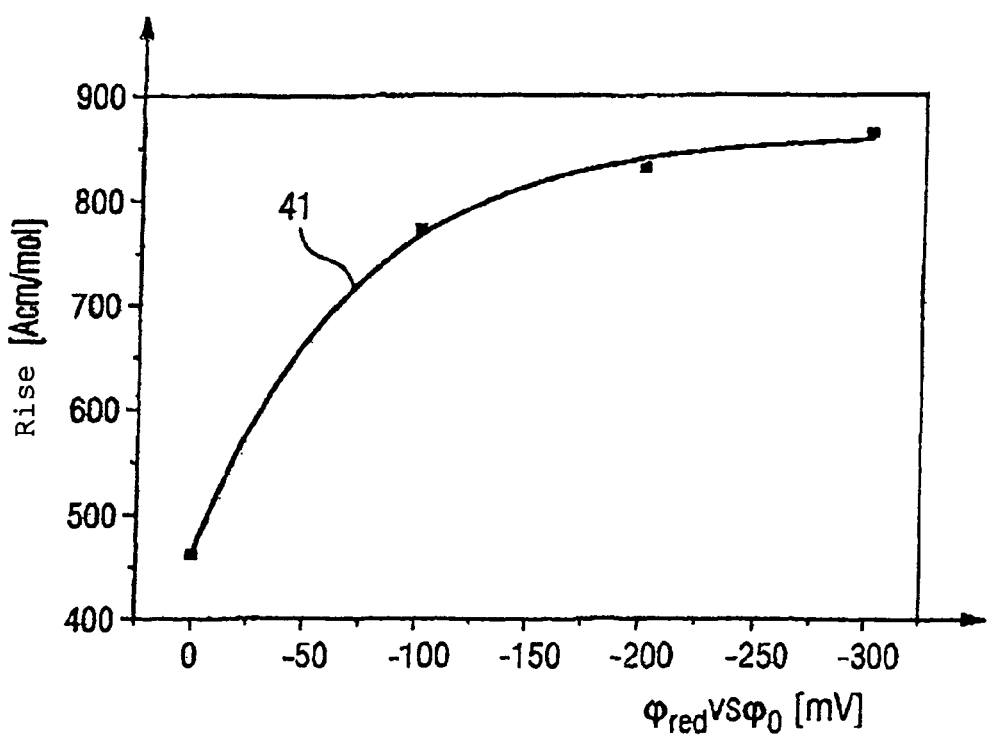
FIG. 4 shows a graphic representation of the rise as a function of the potential during the relaxation phase.

FIG. 3 shows the current density as a function of the pAP concentration in the solution for various pulse trains that are characterised by characteristic lines 31 to 34. The measuring phase always amounts to 0.25 s, the relaxation phase to 0.75 s. The measurement of current takes place 0.24 s after the start of the measuring phase. The oxidation potential during the measuring phase relative to the redox potential amounts to +200 mV. The potential has been varied during the relaxation phase. It assumes values between –300 mV and 0 mV relative to the redox potential. In particular:

$\phi_{red}/\phi_{ox}$ is –300 mV/200 mV for characteristic line 31
–200 mV/200 mV for characteristic line 32
–100 mV/200 mV for characteristic line 33
and 0 mV/200 mV for characteristic line 34.

Given these parameters, different rises in the current density 5 in terms of its functional dependence upon the concentration pAP result.

The rise in the current density with the pAP-concentration, that is, the sensitivity of the measurement, increases constantly with a potential that is becoming negative during the relaxation phase. Plotting the rise against the relaxation potential in accordance with FIG. 4 clearly shows, by way of characteristic line 41, the advantageous effect of pulsed redox-cycling.

Whilst in the case of a relaxation potential of 0 V versus $\phi_0$ the rise only amounts to 462 Acm/mol, this value increases to 864 Acm/mol at –300 mV versus $\phi_0$. This doubling is due to the improved effect of the redox-cycling, because given a relaxation potential of –300 mV versus $\phi_0$ the quinonimine in front of the electrode is completely reduced to para-aminophenol (pAP). Given a relaxation potential of 0 V versus $\phi_0$, on the other hand, in accordance with the Nernst equation directly in front of the electrode a concentration ratio of para-aminophenol:quinonimime=1:1 is set. The quinonimine is thus only partly further reduced.

The rise in sensitivity is only one advantage of pulsed redox-cycling. The constancy of the current signal already during the first seconds of measurement is a further important advantage.

The current density that has set in after a comparatively long measuring time was used to determine the sensitivity. When measuring enzyme activities, for example, the measurement is, however, effected in such a way that the solution is first stirred further or pumped. The pAP formed by the enzyme is rinsed away as a result and a constant basic current sets in. Then the pump is stopped and the rising concentration is measured during the first seconds. Typical rises then lie in the order of magnitude of 2 μA/cm$^2$s. If the measurement itself now results in a drop in the signal, both effects are superimposed and too small a rise in the current and thus in the enzyme activity is measured. Since this drop in the current as a result of the consumption of the substance depends, moreover, upon the concentration thereof, this effect cannot be eliminated by standardization.

Experiments with constant concentration provide information about the signal constancy over time. The concentration amounted to 50 μM pAP, the potential during the measuring phase to +200 mV. The duration of the measuring phase amounted to 250 ms, in which case the measurement of current took place after 240 ms. The potential during the relaxation phase amounted in the first experiment to 0 V versus $\phi_0$, in the second experiment to –300 mV versus $\phi_0$. The duration of the relaxation phase was varied between 250 ms and 4.75 s.

The dependence of the current density j upon time is reproduced in FIG. 5 in a graphic representation. Characteristic lines 51 to 54 result for different relaxation-phase durations $\Delta t_{red}$, that is, in particular between 0.255 and 4.755. The currents fall greatly within the first 10 s of measurement. Given a length of the relaxation phase of 0.25 s, the decrease amounts to 14 μA/cm² in 10 s. If the duration of the relaxation phase is increased to 4.75 s, the decrease in the signal reduces to 9 μA/cm² in 10 s. The shorter the duration of the relaxation phase is therefore, the greater this decrease in the signal is with time. However, even with long relaxation times, the decrease of 0.9 μA/cm² is still considerable compared with the rises that are to be measured in the application in the order of magnitude of 2 μA/cm²s.

If the potential is now reduced during the relaxation phase to −300 mV, the signal constancy is significantly improved. This follows in particular from FIG. 6 which shows a representation that corresponds to FIG. 5 with characteristic lines 61 to 64 for the same parameters of the relaxation phases $\Delta t_{red}$.

Given a relaxation time of 0.25 s, the signal drop still amounts to 8 μA/cm² in 10 s. With a relaxation time of 0.75 s, this value still amounts to 2 μA/cm² in 10s, with 1.75 still 1 μA/cm² in 10 s and for 4.75 s only 0.5 μA/cm² in 10 s. Already with a relaxation time of 0.75 s, that is, a measuring frequency of 1 Hz, and a relaxation potential of −300 mV, the signal drop and thus the error as well only amount to approximately 1% of the expected measured value.

The experiments show the influence of the duration and potential of the relaxation phase on the measuring signal. Simulation calculations can provide further information on the effect of pulsed redox-cycling. In this connection, on the one hand, the current density is calculated in the case of redox-cycling and, on the other hand, the current density without redox-cycling is determined for comparison purposes.

For the simulations with redox-cycling it was assumed that the electrolyte space has a thickness of 100 μm. Both the oxidation potential and the reduction potential are selected so that the reaction occurs in the diffusion limiting current range, that is, the currents are at a maximum. The pulse lengths are 250 ms at the oxidation potential and 750 ms at the reduction potential. In the calculations without redox-cycling, the parameters were the same apart from the fact that during the relaxation phase no potential is predetermined and no current can flow by way of the potentiostat. During this time, the system is therefore decoupled electrochemically.

The comparison of the simulation data is effected with the experimental results for the corresponding pulse lengths and the potentials $\phi_{ox}$=+200 mV and $\Delta_{red}$=−300 mV. These potential limits correspond best of all to the stipulations for the simulation. The y-axis sections of the simulation data were adapted to the experimental results.

FIG. 7 shows good correspondence between the experiment and simulation for pulsed redox-cycling, with 71 representing the measured values and 72 representing the calculated characteristic lines. The drop in the current density is small under these conditions with 2 μA/cm² in 4 s. Without redox-cycling, on the other hand, the drop in current density during the first 4 s already amounts to 12 μA/cm², this being illustrated by the characteristic line 73. The results for pulsed redox-cycling with potentiostat-operation during the relaxation phase at redox potential lie in between, this being reproduced by characteristic line 74.

The improvement in the signal constancy by the factor 6 can be directly attributed to the concentration profiles. The following representation shows the calculated concentration profiles of pAP as a function of the spacing of the electrode, as they appear at the end of the 5th relaxation phase.

In the case of pulsed redox-cycling, during the relaxation phase, the previously formed oxidation product is reduced again. Consequently, the concentration of pAP directly in front of the electrode at the end of the relaxation phase has risen back to the original value $c_\infty$. Further away from the electrode, the concentration is only slightly diminished. Without redox-cycling, on the other hand, the concentration in front of the electrode immediately before the next measuring phase only amounts to 38%. Also further away from the electrode, the concentration is clearly lower.

This follows in particular from FIG. 8 with characteristic lines 81 and 82. In this connection, the example, in accordance with characteristic line 82 for measurement without redox-cycling, in practice corresponds to the measurement of the concentration of a substance which can admittedly be oxidized, yet whose oxidation products cannot be reduced again. The case would also be similar for a substance that reduces, but whose reduction products cannot be oxidized again. In the case of a biochemical sensor, this could, for example, be naphthol, which like pAP as well can be released during an enzymatic reaction.

Figure 9:
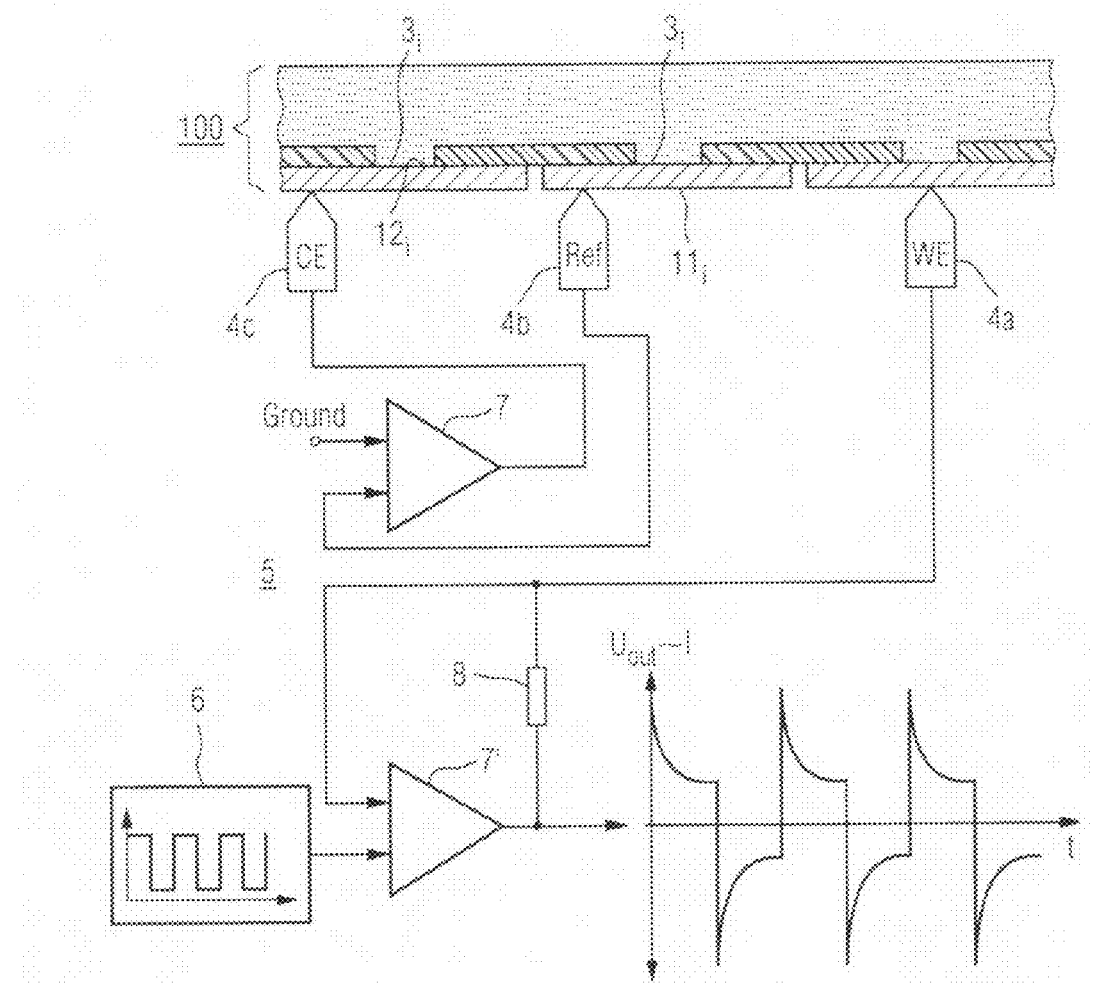
FIG. 9 shows a measuring device for pulsed redox-cycling with an associated transducer array.

The measuring device can be seen in detail in FIG. 9. Apart from being realized by way of a transducer array 100 which is described further in detail with the aid of FIGS. 10 and 11, the measuring device is substantially realized by way of a suitable potentiostat 5 in combination with a pulse generator 6 which delivers optionally rectangular, triangular or sinusoidal pulses. By way of two operational amplifiers 7 and 7', of which one is connected to ground potential, and a defined measuring resistor 8, the potentiostat 5 is conceived in such a way that suitable potentials are provided. In this connection, the pulse length, the repetition rate and the level of the potential can be predetermined. In particular, the pulse lengths of the measuring phases and the relaxation phases can be set separately and be of different lengths. The potentials can also be of different magnitudes.

Associated with the transducer array 100 there are individual electrodes 4a-4c which, in accordance with the intended purpose, realize a reference electrode REF 4b, a counter electrode CE 4c and at least one measuring or working electrode WE 4a. These electrodes are connected to the potentiostat 5 as a three-electrode arrangement. The signal of the potentiostat 5 is linked up to a signal-processing unit, which is not shown in detail in FIG. 9, with which evaluation takes place in consideration of the above statements regarding measuring methodology and accuracy. Generally, the signal pattern shown in FIG. 9 as $U_{out}$ results for the evaluation.

FIG. 9, with which evaluation takes place in consideration of the above statements regarding measuring methodology and accuracy. Generally, the signal pattern shown in FIG. 9 as $I_{out}$ results for the evaluation.

The transducer array 100 is reproduced in FIGS. 10/11 as part of the measuring device that is planar and flexible and in particular can be produced inexpensively as well. What is important in this connection is that now it is possible to carry out measurements for pulsed redox-cycling with one simplified transducer array 100. FIGS. 10 and 11 show the upper $12_i$ and lower side $11_i$ of the transducer array 100—consisting of a metal substrate 1 and an insulator layer 2. Circular depressions $3_i$ that are referred to as cavities are shown on the upper side, for example. The cavities $3_i$ develop as a result of the structuring of the insulator 2. The upper side $12_i$ of the metal substrate 1 lies open at the base of the depressions $3_i$ and forms a measuring point, if an analytical unit is applied.

The representation of the rear side shows by way of lines a structuring and thus a sectioning of the metal substrate 1 into portions that are isolated from each other. Each metal island corresponds with a depression $3_i$ on the front side. The possible contact points for a so-called needle card for simplified electrical contacting of the metal surfaces are indicated by dots. What is important in this connection is that a plurality of metal islands, preferably three, with an analytical unit define a sensor, and with the associated electrodes 15, that is, a measuring electrode WE 4a, a counter electrode CE 4c and a reference electrode REF 4b, are suitable for carrying out electrochemical measurements.

Further specific electrode arrangements are described in a parallel application with the title "Elektrochemisches Transducer-Array und dessen Verwendung", belonging to the applicant and having the same filing priority.

A biochemical sensor for DNA analysis is realized with an arrangement in accordance with FIG. 9 and a transducer array 100 in accordance with FIGS. 10/11, for example. The transducer array 100 that is described with the aid of FIGS. 10/11 and consists of a metal layer and an insulator layer that is connected therewith and has cavities $3_i$ is used. The diameter of the cavities $3_i$ amounts to 0.8 m, the depth to 90 μm and the spacing between two adjacent electrodes to 1 mm. The electrode surfaces are covered with a 2.3 μm thick gold layer.

All in all, in at least one example embodiment, the sensor arrangement consists of four electrodes for this intended application. One of the electrodes as a reference electrode is coated with a silver/silver chloride (Ag/AgCl)-layer, another electrode is used as a counter electrode CE and the two further electrodes serve as measuring electrodes WE.

On one of the measuring electrodes a synthetic oligonucleotide sequence of length 25 is anchored by way of a terminal thiol group on the gold surface as a positive test unit. The second measuring electrode remains free as a negative test unit. Then both surfaces are incubated with a solution of 1 mg bovine serum albumin per ml for 15 minutes and subsequently the sensor array is inserted into a 100 μm deep through-flow channel. In the first instance 10 μl of a 10 μM biotinylated target sequence is pumped over the electrodes within approximately 5 minutes. Then after a washing step, a solution of streptavidine of marked alkaline phosphatase is passed thereover.

Washing is effected with a buffer solution of 100 mM tris(hydroxymethyl)aminomethane titrated to pH 8 with hydrochloric acid, 130 mM NaCl. After repeated washing, a 2 mM solution of the enzyme substrate para-aminophenylphosphate (pAPP) in the buffer solution is pumped over the sensor array. In the presence of the enzyme alkaline phosphatase, the enzyme substrate pAPP is converted into para-aminophenol (pAP).

The reference electrode RE, counter electrode CE and in each case one of the two measuring electrodes WE are each connected to a potentiostat in a three-electrode arrangement. The measurement is effected by way of pulsed redox-cycling. During the measuring phase, the para-aminophenol formed by the enzyme is oxidized to form quinonimine. The oxidation potential $\phi_{ox}$ amounts to +200 mV versus $\phi^0$. In the relaxation phase, the quinonimine that is formed is reduced back to para-aminophenol at $\phi_{red}=-200$ mV. The pulse length of the measuring phase amounts to 250 ms, that of the relaxation phase to 750 ms. The current is measured 240 ms after the start of the measuring phase.

At the beginning of the experiment, the positive test unit, that is, the electrode with the catcher sequence, is connected. The solution with the enzyme substrate flows—conveyed by a pump—in the first instance over the negative test unit and then over the positive test unit. As a result of the flow movement, pAP formed by the enzyme is rinsed away from the electrodes so that when the pump is switched on the current is constant and low. If the pump is now stopped, the pAP concentration rises as a result of the enzyme activity with time. In the measurement, this is shown by a great rise in the current signal with 20 nA/s. If the pump is switched on again, the signal drops back to the original value. This process can be repeated as often as desired.

FIG. 12 shows the course of the current over time with the pump "on"/"stop" at the sensor arrangement that has been described with a positive and a negative test unit. The characteristic line 121 shows the course of the pump current. A specific course with individual peaks ensues for the experiment, with parameters the activation of the pump on the one hand ("stop"/"on") and the switch-over of the measuring electrodes, on the other hand. The measuring range of interest is shown underneath in each case in broken lines.

When t=400 s, there has been a switch-over to the negative test unit. Here the current drops in the first instance when the pump is stopped, then remains constant for a short time, and then slowly rises. This rise is brought about by the diffusion of pAP from the positive to the negative test unit. With the pump "on", a peak current appears, since the electrolyte first flows from the positive to the negative test unit and thus an increased pAP-concentration is transported to the adjacent electrode. All in all, the discrimination between the positive and negative test unit is very good.

In an alternative measuring arrangement of at least one embodiment, instead of the self-supporting and flexible transducer array in accordance with FIGS. 9 to 11, a transducer array with the use of thin-film technology on a rigid substrate is employed. In this connection, areal electrodes are provided that have an extent that is greater than the length of diffusion. A typical diffusion length for the example specified above amounts to 25 μm so that the areal electrodes have an extent $\geq 30$ μm, preferably $\geq 50$ μm.

The rigid substrate is in particular silicon, which is preferably provided with an insulator layer.

It is also possible to carry out the redox-cycling in accordance with at least one embodiment of the invention with such transducers that enable CMOS technology to be accessed for signal-processing.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:
1. A method for measuring at least one of a concentration and change in concentration of a redox-active substance as a mediator in a molecular-biological detection system, in which as a result of application of suitable potentials to a working electrode, at least one of a reduction process and an oxidation process takes place as a redox reaction, the method comprising:
measuring an oxidation current to obtain a measuring phase;
measuring a reduction current to obtain a relaxation phase;
pulsing the potential of the working electrode, and alternately forming the measuring phases and the relaxation phases;
selecting measuring-phase pulse lengths so that, at the end of the pulse, a capacitive current is small in comparison with a Faraday current; and
selecting relaxation-phase pulse lengths so that, at the end of the pulse, a concentration gradient is relaxed such that at a beginning of a following measuring phase, the change in concentration of the mediator, brought about by the measurement of the mediator, is reversible.

2. The method according to claim 1, wherein a current, measurable at the end of the measuring phase, forms the measuring signal.

3. The method according to claim 1, wherein the potentials are selected so that the reactions occur in a diffusion limiting current range.

4. The method according to claim 1, further comprising:
measuring at least one of a concentration and change in concentration of a redox-active substance as a mediator, in a molecular-biological detection system, using the selected pulse lengths.

5. The method according to claim 1, wherein, when measuring the reduction current, an oxidation potential is set during the relaxation phase and the species reduced during the measuring phase and still located in front of the working electrode are oxidized again.

6. The method according to claim 5, wherein the pulsed redox-cycling is carried out with set pulse shapes.

7. The method according to claim 6, wherein the pulsed redox-cycling is carried out with at least one of a rectangular, triangular and sinusoidal course.

8. The method according to claim 1, wherein the relaxation phase is at least as long as the measuring phase.

9. The method according to claim 8, wherein the relaxation phase is longer than the measuring phase.

10. The method according to claim 9, wherein, with a repetition rate of 1 Hz, the pulse lengths of the measuring phases amount to 100 to 300 ms, and the relaxation phase amounts to between 700 and 900 ms.

11. The method according to claim 9, wherein, with a repetition rate of 1 Hz, the pulse lengths of the measuring phases amount to 250 ms, and the relaxation phase amounts to 750 ms.

12. The method according to claim 1, wherein, when measuring the oxidation current, a reduction potential is set during the relaxation phase and the species oxidized during the measuring phase and still located in front of the working electrode are reduced again.

13. The method according to claim 12, wherein the repetition rate for the pulsed redox-cycling amounts to at least 1/10 Hz.

14. The method according to claim 12, wherein the repetition rate for the pulsed redox-cycling amounts to at least 1/10 Hz.

15. The method according to claim 12, wherein the pulsed redox-cycling is carried out with set pulse shapes.

16. The method according to claim 15, wherein the pulsed redox-cycling is carried out with at least one of a rectangular, triangular and sinusoidal course.

* * * * *